United States Patent [19]

Matsumoto et al.

[11] Patent Number: 4,886,810
[45] Date of Patent: Dec. 12, 1989

[54] QUINOLINE DERIVATIVES, PHARMACEUTICAL COMPOSITION AND METHOD OF USE

[75] Inventors: Jun-ichi Matsumoto, Ikoma; Teruyuki Miyamoto, Sakai; Hiroshi Egawa, Toyonaka; Shinichi Nakamura, Takatsuki, all of Japan

[73] Assignee: Dainippon Pharmaceutical Co., Ltd., Osaka, Japan

[21] Appl. No.: 42,806

[22] Filed: Apr. 27, 1987

[30] Foreign Application Priority Data

Apr. 25, 1986 [JP] Japan .................. 61-97543

[51] Int. Cl.⁴ ............... A61K 31/47; C07D 401/04
[52] U.S. Cl. ........................... 514/312; 544/363; 546/156
[58] Field of Search .......... 544/363; 546/156; 514/254, 312

[56] References Cited

U.S. PATENT DOCUMENTS

| | | | |
|---|---|---|---|
| 4,556,658 | 12/1985 | Grohe et al. | 514/254 |
| 4,657,913 | 4/1987 | Mitch et al. | 514/278 |
| 4,665,079 | 5/1987 | Culbertson et al. | 544/363 |
| 4,668,680 | 5/1987 | Trehan et al. | 544/363 |
| 4,771,054 | 9/1988 | Domagala et al. | 544/363 |
| 4,771,055 | 9/1988 | Domagala et al. | 546/156 |

FOREIGN PATENT DOCUMENTS

| | | |
|---|---|---|
| 172651 | 2/1986 | European Pat. Off. |
| 202763 | 11/1986 | European Pat. Off. |
| 0221463 | 5/1987 | European Pat. Off. ............ 544/363 |
| 0255908 | 2/1988 | European Pat. Off. ............ 546/156 |
| 85/2369 | 3/1985 | South Africa . |

OTHER PUBLICATIONS

Derwent World Patent Index, Accession No. 83-823272/47, Abstracting Japanese JP058509, Apr. 7, 1982.

*Primary Examiner*—Glennon H. Hollrah
*Assistant Examiner*—James H. Turnipseed
*Attorney, Agent, or Firm*—Wenderoth, Lind & Ponack

[57] ABSTRACT

The present invention relates to quinoline derivatives of the formula

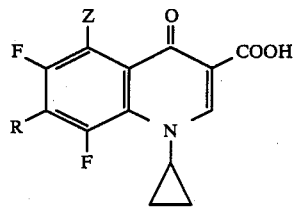

(I)

wherein Z is an amino group or a halogen atom, R is

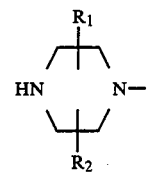

(A)

or

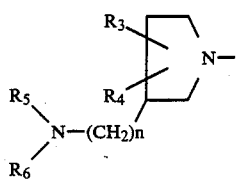

(B)

in which $R_1$ is a hydrogen atom, a lower alkyl or haloalkyl group, $R_2$ is a hydrogen atom or a lower alkyl group, $R_3$ is a lower alkyl or haloalkyl group, $R_4$ is a hydrogen atom or a lower alkyl group, $R_5$ and $R_6$ are the same or different and each represents a hydrogen atom or a lower alkyl group, or $R_5$ and $R_6$, together with the nitrogen atom to which they are attached, form a heterocyclic ring, and n is 0 or 1, with the proviso that when Z is an amino group, R is (B);

and esters thereof and salts thereof and processes for preparation thereof. These compounds show excellent antibacterial activity and are useful antibacterial agents.

10 Claims, No Drawings

QUINOLINE DERIVATIVES, PHARMACEUTICAL COMPOSITION AND METHOD OF USE

This invention relates to novel quinoline compounds having very high antibacterial activity, and processes for preparing these compounds.

The compounds of this invention are quinoline derivatives represented by the following general formula

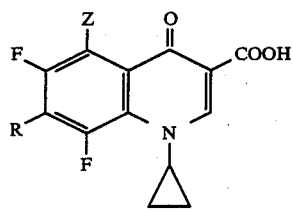

wherein Z is an amino group or a halogen atom,

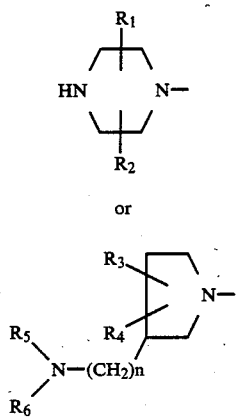

in which
$R_1$ is a hydrogen atom, a lower alkyl or haloalkyl group,
$R_2$ is a hydrogen atom or a lower alkyl group,
$R_3$ is a lower alkyl or haloalkyl group,
$R_4$ is a hydrogen atom or a lower alkyl group,
$R_5$ and $R_6$ are the same or different and each represents a hydrogen atom or a lower alkyl group, or $R_5$ and $R_6$, together with the nitrogen atom to which they are attached, form a heterocyclic ring, and n is 0 or 1, with the proviso that when Z is an amino group, R is (B); or esters thereof, or salts of said compounds or esters.

The salts of the compounds of formula (I) or their esters may be any salts formed from the compounds of formula (I) or their esters with pharmaceutically acceptable acids or bases. The salts of the compounds of the invention are the salts derived from inorganic acids such as hydrochloric acid or phosphoric acid; those from organic acids such as acetic acid, lactic acid, oxalic acid, succinic acid, methane sulfonic acid, maleic acid, malonic acid, or gluconic acid; those from acidic amino acids such as aspartic acid or glutamic acid; metal (e.g. sodium, potassium, calcium, magnesium, zinc or silver) salts; those from organic bases such as dimethylamine, triethylamine, dicyclohexylamine or benzylamine; and those from basic amino acids such as lysine or arginine.

The esters of the compounds of formula (I) include not only substituted or unsubstituted aliphatic esters, especially lower alkyl esters such as methyl or ethyl esters, but also esters that can be at least partially converted to the compounds (I) by chemical hydrolysis or by enzymatic hydrolysis in vivo, such as acetoxymethyl esters, pivaloyloxymethyl esters, ethoxycarbonyloxyethyl esters, choline esters, aminoethyl esters (e.g., dimethylaminoethyl or 1-piperidinylethyl esters), 5-indanyl esters, phthalidyl esters, and hydroxyalkyl esters (e.g., 2-hydroxyethyl or 2,3-dihydroxypropyl esters).

The term "lower", as used in the present specification and the appended claims to qualify groups or compounds, means that the groups or compounds so qualified have not more than 6, preferably not more than 4 carbon atoms.

The compounds of formula (I), their esters, and salts of these compounds will therefore be generically referred to herein as the compounds of this invention.

The compounds of the invention may also exist as hydrates. Hence, these hydrates are also included in the compounds of this invention.

The compounds of the invention include those which have asymmetric carbon atoms on the piperazine or pyrrolidine ring at the 7-position and therefore exist in optically active forms. Hence, D isomers, L isomers and mixtures thereof are all included in the compound of this invention.

Some of the compounds of this invention have two asymmetric carbon atoms on the piperazine or pyrrolidine ring at the 7-position and therefore can exist as stereoisomers having different configurations (cis or trans form). These stereoisomers and their mixtures are also included within the compounds of this invention.

The prior art on pharmaceutically effective compounds in this field will be discussed below.

Japanese Laid-Open Patent Publication No. 174367/1983 (an abstract of which is disclosed in Derwent World Patent Index, Accession No. 83-823272) discloses that compounds represented by the general formula (10)

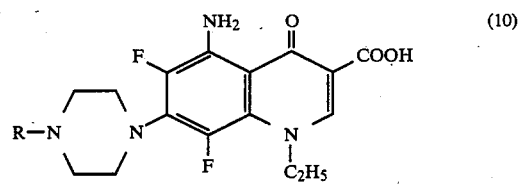

wherein R represents a hydrogen atom or a lower alkyl group,
have antibacterial activity. However, the compounds of the present invention have higher antibacterial activity than the above known compounds.

South African Laid-Open Patent Specification No. 8502369 discloses the following general formula (11)

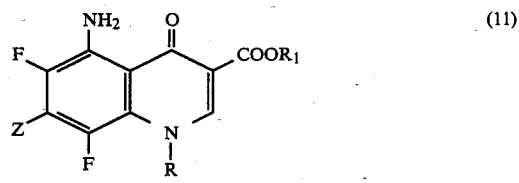

The specification does not disclose a cyclopropyl group as the group R in formula (11).

European Laid-Open Patent Specifications Nos. 172651 202763 disclose compounds represented by the following general formula (12)

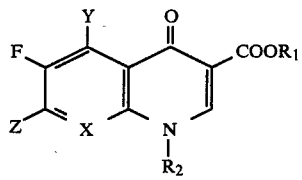
(12)

wherein Y is an amino group or a fluorine atom. The specifications do not disclose such a group as described in this invention as the group Z in formula (12).

U. S. Pat. No. 4,556,658 discloses compounds represented by the following general formula (13)

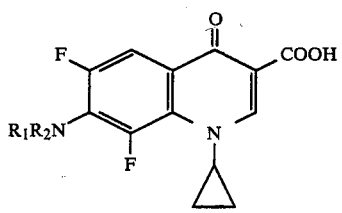
(13)

They, however, do not have an amino group or a halogen atom at the 5-position of the quinoline ring as is clearly seen from formula (13).

It is an object of this invention to provide novel quinoline derivatives of formula (I) having high antibacterial activity against both Gram-positive bacteria and Gram-negative bacteria, esters thereof, and pharmaceutically acceptable salts of these, and processes for preparing these novel compounds.

Another object of this invention is to provide a pharmaceutical composition comprising an effective amount of a compound of formula (I), an ester thereof, or a pharmaceutically acceptable salt of any of these.

The invention further provides a method of treating bacterial infectious diseases of warm-blooded animals, which comprises administering the compounds or the pharmaceutical composition of this invention.

These and other objects of the invention will become apparent from the following description.

The typical compounds of this invention include the following compounds.

1-Cyclopropyl-5,6,8-trifluoro-7-(3-methyl-1-piperazinyl)-1,4-dihydro-4-oxoquinoline-3-carboxylic acid of the formula:

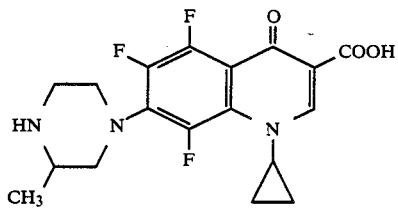

1-Cyclopropyl-5,6,8-trifluoro-7-(1-piperazinyl)-1,4-dihydro-4-oxoquinoline-3-carboxylic acid of the formula:

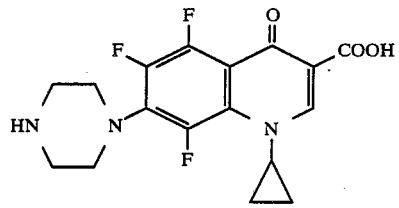

1-Cyclopropyl-5,6,8-trifluoro-7-(3,5-dimethyl-piperazinyl)-1,4-dihydro-4-oxoquinoline-3-carboxylic acid of the formula:

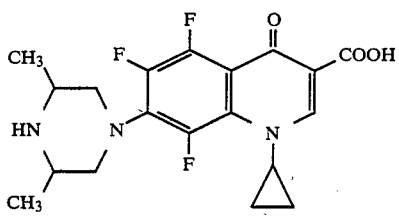

1-Cyclopropyl-5,6,8-trifluoro-7-(3-fluoromethyl-1-piperazinyl)-1,4-dihydro-4-oxoquinoline-3-carboxylic acid of the formula:

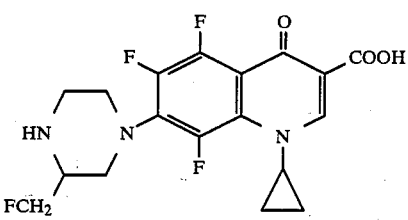

7-(3-Amino-3-methyl-1-pyrrolidinyl)-1-cyclopropyl-5,6,8-trifluoro-1,4-dihydro-4-oxoquinoline-3-carboxylic acid of the formula:

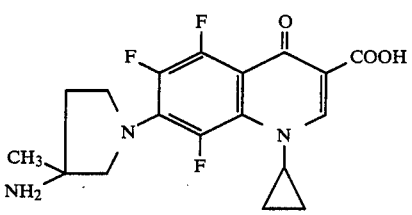

7-(3-Amino-3-ethyl-1-pyrrolidinyl)-1-cyclopropyl-5,6,8-trifluoro-1,4-dihydro-4-oxoquinoline-3-carboxylic acid of the formula:

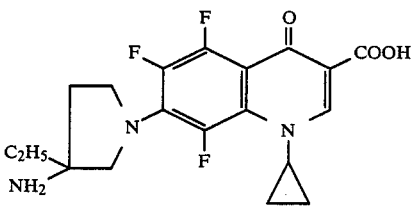

7-(3-Amino-4-methyl-1-pyrrolidinyl)-1-cyclopropyl-5,6,8-trifluoro-1,4-dihydro-4-oxoquinoline-3-carboxylic acid of the formula:

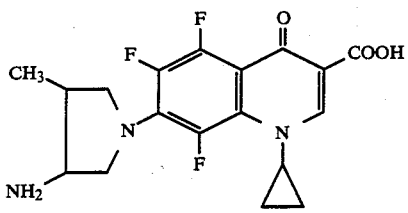

7-(3-Amino-4-ethyl-1-pyrrolidinyl)-1-cyclopropyl-5,6,8-trifluoro-1,4-dihydro-4-oxoquinoline-3-carboxylic acid of the formula:

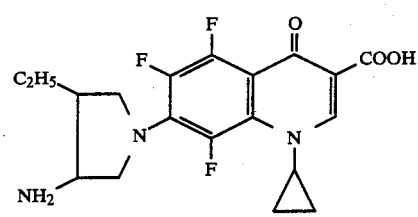

7-(3-Amino-4-fluoromethyl-1-pyrrolidinyl)-1-cyclopropyl-5,6,8-trifluoro-1,4-dihydro-4-oxoquinoline-3-carboxylic acid of the formula:

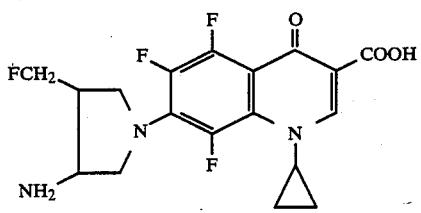

7-(3-Amino-4-fluoromethyl-3-methyl-1-pyrrolidinyl)-1-cyclopropyl-5,6,8-trifluoro-1,4-dihydro-4-oxoquinoline-3-carboxylic acid of the formula:

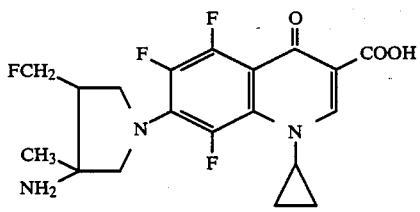

5-Amino-7-(3-amino-3-methyl-1-pyrrolidinyl)-1-cyclopropyl-6,8-difluoro-1,4-dihydro-4-oxoquinoline-3-carboxylic acid of the formula:

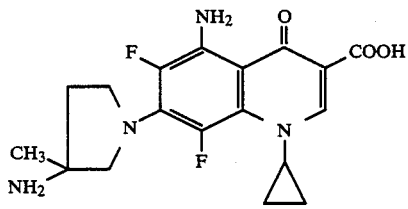

5-Amino-7-(3-amino-4-methyl-1-pyrrolidinyl)-1-cyclopropyl-6,8-difluoro-1,4-dihydro-4-oxoquinoline-3-carboxylic acid of the formula:

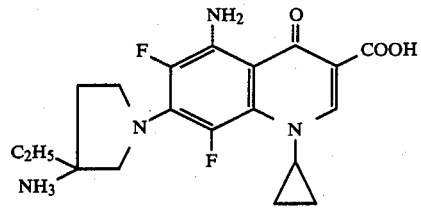

5-Amino-7-(3-amino-4-methyl-1-pyrrolidinyl)-1-cyclopropyl-6,8-difluoro-1,4-dihydro-4-oxoquinoline-3-carboxylic acid of the formula:

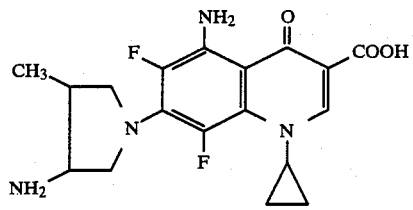

5-Amino-7-(3-amino-4-ethyl-1-pyrrolidinyl)-1-cyclopropyl-6,8-difluoro-1,4-dihydro-4-oxoquinoline-3-carboxylic acid of the formula:

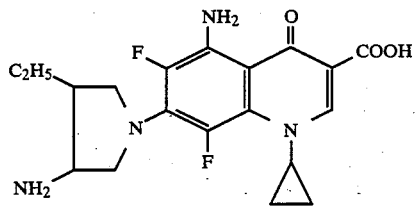

5-Amino-7-(3-amino-4-fluoromethyl-1-pyrrolidinyl)-1-cyclopropyl-6,8-difluoro-1,4-dihydro-4-oxoquinoline-3-carboxylic acid of the formula:

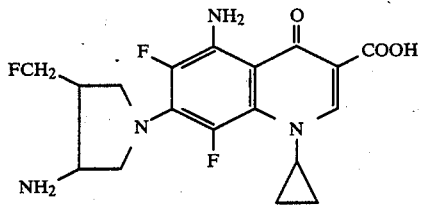

5-Amino-7-(3-amino-4-fluoromethyl-3-methyl-1-pyrrolidinyl)-1-cyclopropyl-6,8-difluoro-1,4-dihydro-4-oxoquinoline-3-carboxylic acid of the formula:

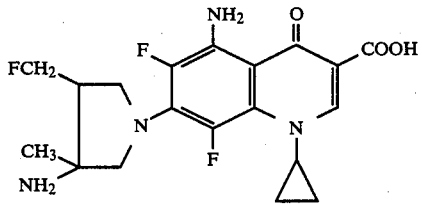

5-Amino-7-(3-amino methyl-4-methyl-1-pyrrolidinyl)-1-cyclopropyl-6,8-difluoro-1,4-dihydro-4-oxoquinoline-3-carboxylic acid of the formula:

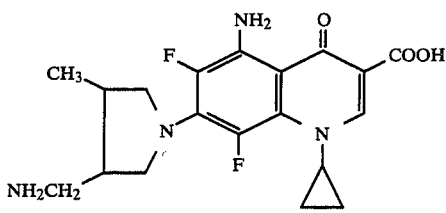

5-Amino-7-(3-aminomethyl-4-ethyl-1-pyrrolidinyl)-1-cyclopropyl-6,8-difluoro-1,4-dihydro-4-oxoquinoline-3-carboxylic acid of the formula:

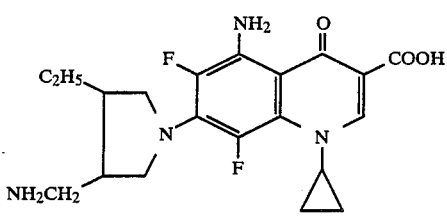

5-Amino-1-cyclopropyl-6,8-difluoro-7-(3-ethyl-4-ethyl aminomethyl-1-pyrrolidinyl)-1,4-dihydro-4-1-oxoquinoline-3-carboxylic acid of the formula:

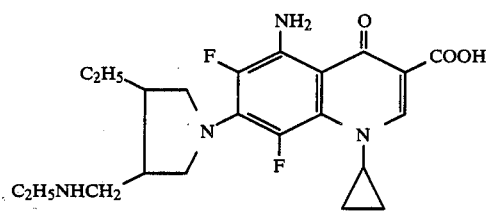

The compounds of this invention show excellent antibacterial activity and a broad antibacterial spectrum in vitro tests. Furthermore, these compounds show an excellent infection-defending effect in vivo on topical or systemic infections caused by Gram-positive and Gram-negative bacteria.

The processes for preparing the compounds of this invention will be described below.

A. Substitution reaction by piperazine derivatives

The compounds of this invention can be produced by reacting a carboxylic acid or its ester (preferably a lower alkyl ester) represented by the following general formula

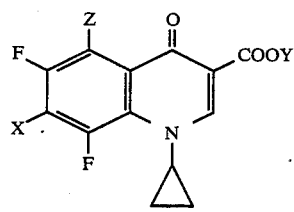

(II)

wherein Z is an amino group or a halogen atom, X is a halogen atom, and Y is a hydrogen atom or an aliphatic group, with the proviso that when Z is a halogen atom, Y is a hydrogen atom, with a compound represented by the following general formula

R—H  (III)

wherein R is as defined with respect to formula (I).

Examples of the halogen atom for X in formula (II) are fluorine, chlorine or bromine atoms.

This reaction can be carried out by stirring the starting compounds (II) and (III) at 10° to 180° C. for 10 minutes to 24 hours in an inert solvent. Examples of the inert solvent include alcohols such as ethanol, ethers such as dioxane, tetrahydrofuran and 1,2-dimethoxyethane, aromatic hydrocarbons such as benzene, toluene and xylene, acetonitrile, dimethylformamide, dimethyl sulfoxide, pyridine and water.

Generally, the above reaction is carried out in the presence of an acid acceptor using the starting compound of formula (III) in an amount equivalent or slightly excessive with regard to the starting compound (II). If desired, the starting compound (III) may be used in excess to make it serve concurrently as the acid acceptor. Examples of the acid acceptor are sodium hydrogen carbonate, sodium carbonate, potassium carbonate, triethylamine, 1,8-diazabicyclo5.4.0]undecene-7 (DBU), pyridine, and picoline.

The starting compound (III) used in this reaction may, if possible, be used in a protected form, and after the reaction, its protective group is removed in a customary manner. The protective group may be any protective group which can be removed without destroying structure of the compounds of this invention formed by the reaction. Groups which are normally used as protective groups for the amino group in the field of chemistry of peptides, aminosugars, nucleic acids or beta-lactam compounds may be used in this invention.

The amino protective groups may be split off by solvolysis (including hydrolysis) or hydrogenolysis depending upon the properties of the protective groups.

Specific examples of the protective groups capable of being eliminated by solvolysis include acyl groups such as formyl, acetyl and trifluoroacetyl; substituted or unsubstituted alkoxycarbonyl groups such as ethoxycarbonyl, t-butoxycarbonyl, benzyloxycarbonyl, p-methoxybenzyloxycarbonyl and beta-(p-toluenesulfonyl)ethoxycarbonyl; a trityl group; a trimethylsilyl group; an o-nitrophenylsulfenyl group; a diphenylphosphinyl group; and a tetrahydropyranyl group.

This reaction is carried out in a solvent at 0° to 150° C. in the presence or absence of a catalyst such as an acid or base.

Examples of the acid are inorganic acids such as hydrochloric acid, hydrobromic acid, sulfuric acid and phosphoric acid; organic acids such as acetic acid, trifluoroacetic acid, formic acid, and toluenesulfonic acid; Lewis acids such as boron tribromide and aluminum chloride. Examples of the base are metal hydroxides such as sodium hydroxide and barium hydroxide, alkali metal carbonates such as sodium carbonate and potassium carbonate; alkali metal alkoxides such as sodium methoxide and sodium ethoxide; and sodium acetate. Usually, water is used as the solvent. Depending upon the property of the compound, another solvent such as ethanol, dioxane, ethylene glycol dimethyl ether, benzene or acetic acid, or a mixed solvent of such a solvent with water may be used.

Examples of protective groups that may be eliminated by hydrogenolysis include arylsulfonyl groups such as p-toluenesulfonyl; a methyl group substituted by phenyl or benzyloxy, such as benzyl, trityl or benzyloxymethyl; arylmethoxycarbonyl groups such as benzyloxycarbonyl and p-methoxybenzyloxycarbonyl; and halogenoethoxycarbonyl groups such as beta,beta,beta-trichloroethoxycarbonyl and beta-iodoethoxycarbonyl groups.

This reaction uses different reaction conditions depending upon the property of the protective group to be eliminated. For example, it is carried out by treating the compound with a hydrogen stream in an inert solvent at 10° to 60° C. in the presence of a catalyst such as platinum, palladium or Raney nickel; or treating it with metallic sodium in liquid ammonia usually at −50° to −20° C.; or by treating it with a metal such as zinc in acetic acid or in an alcohol such as methanol. Examples of the solvent in the catalytic reduction may include ethylene glycol dimethyl ether, dioxane, dimethylformamide, ethanol, ethyl acetate and acetic acid.

The starting compound (II) can be prepared by the methods described in Referential Examples 1 and 2 or methods substantially in accordance with them.

B. Amination reaction

The compounds of this invention can be prepared by reacting a carboxylic acid or its ester (preferably a lower alkyl ester) represented by the following general formula

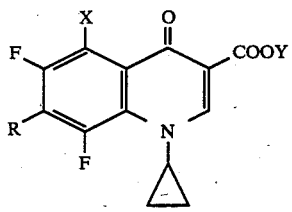

(IV)

wherein R, X and Y are as defined above, with ammonia.

This reaction can be carried out by contacting the starting compound (IV) with ammonia for 1 to 50 hours at a temperature of 50° to 150° C. in an inert solvent, for example an alcohol such as ethanol, pyridine, dimethylformamide or water, preferably in a sealed tube.

This reaction is carried out in the presence of an acid acceptor using ammonia in an amount equivalent to, or slightly in excess of, the starting compound (IV). Conveniently, ammonia is used in excess to make it serve also as the acid acceptor. A salt such as ammonium acetate may be caused to act instead of ammonia.

The starting compound (IV) used in this reaction may, if possible, be used in a form protected with such a protective group as described above in regard to process variant A, and after the reaction, the protective group is eliminated in a customary manner.

The starting compound (IV) is novel and can be prepared by the process variant A above or the process variant D below.

C. Splitting off of the 5-amino protective group

The compound of this invention can be prepared by solvolyzing (also hydrolyzing) or hydrogenolyzing a compound represented by the following general formula

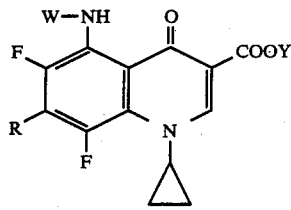

(V)

wherein W is an amino-protective group, and R and Y are as defined hereinabove.

Examples of the amino-protective group W in formula (V) include acyl groups such as formyl, acetyl and trifluoroacetyl; alkoxycarbonyl groups such as methoxycarbonyl, ethoxycarbonyl and benzyloxycarbonyl; substituted methyl groups such as benzyl and benzhydryl; and a benzyloxy group.

This reaction is carried out in the same way as described hereinabove with regard to the elimination of the amino-protective group in the process variant A.

The starting compound (V) used in this reaction may, if possible, be used in a form protected with such a protective group as is described with regard to the process variant A, and after, or simultaneously with, the present reaction, the protective group is eliminated in a customary manner.

The starting compound (V) is a novel compound, and can be prepared by the methods described in Referential Examples 3 and 4 below, or methods substantially in accordance with them.

D. Cyclization of β-Aminoacrylate

The compound of this invention can also be produced by cyclizing a β-aminoacrylate represented by the following general formula

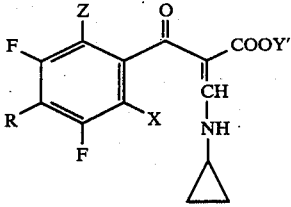

(VI)

wherein Y' is an aliphatic group, and R, X and Z are as defined above,
in the presence of a base, and if required, hydrolyzing the product.

This reaction can be carried out by intramolecularly cyclizing the starting compound (VI) in an inert solvent such as ethanol, isopropanol, t-butanol, dioxane, dimethylformamide, dimethyl sulfoxide and N-methylpyrrolidone in the presence of a base, for example an alkali metal hydroxide such as sodium or potassium hydroxide, an alkali metal carbonate such as sodium or potassium carbonate, an alkali metal bicarbonate such as sodium or potassium bicarbonate, sodium hydride, sodium ethoxide, potassium t-butoxide, butyllithium, triethylamine, or 1,8-diazabicyclo[5.4.0]undecene-7 (DBU). The reaction temperature is usually −20° to 150° C.

The starting compound (VI) used in this reaction may, if possible, be used in a form protected with such a protective group as described above in regard to process variant A, and after the reaction, the protective group is eliminated in a customary manner.

The starting compound (VI) can be prepared by the method described in Referential Example 5 or methods substantially in accordance with it.

Where the compounds of this invention obtained by the above processes are esters, they can be converted to compounds of formula (I) by hydrolyzing the ester moiety in a customary manner. If required, the compounds of formula (I) may be esterified in a customary manner to form esters of the compounds of formula (I).

Pharmaceutically acceptable salts of the compounds of formula (I) or their esters may be produced by treating the compounds of formula (I) or esters thereof with acids, or by treating the compounds (I) with bases or metal salts. Acids suitable for salt formation include, for example, hydrochloric acid, phosphoric acid, acetic acid, lactic acid, oxalic acid, succinic acid, methane sulfonic acid, maleic acid, malonic acid, gluconic acid, aspartic acid and glutamic acid. Bases or metal salts suitable for salt formation include, for example, metal hydroxides such as sodium hydroxide and potassium hydroxide, metal carbonates such as sodium carbonate and potassium carbonate, zinc chloride, zinc sulfate, zinc nitrate and silver nitrate.

The compounds of this invention prepared as stated above are isolated and purified in a customary manner, and depending upon the isolating and purifying conditions, may be obtained in the form of a salt or the free form. They may be converted into each other to produce the compounds of this invention in the desired forms.

The stereoisomers (cis and trans forms) of the compounds of this invention can be isolated by a conventional method such as fractional crystallization or chromatography. It is possible to produce compounds of this invention having a cis or trans configuration by the process variant A described above using the starting compounds (III) having a cis or trans configuration.

The optically active isomers of the compounds of this invention can be separated by known methods.

The compounds (I) thus obtained, their esters, and salts of these are all new compounds. In particular, the compounds (I) and their salts are valuable as antibacterial agents since they have very high antibacterial activity. The compounds (I) and their salts can be used not only as medicines for human and animals, but as fish medicines, agricultural chemicals and food preservatives. The esters of the compounds (I) are of course valuable as starting materials for synthesizing the compounds (I). When the esters can be easily transformed into the compounds (I) in vivo, they can exhibit an equivalent effect and are also useful as antibacterial agents.

Compounds (I) of this invention have excellent antibacterial activity, low toxicity, good absorbability and good metabolism stability and are therefore useful as antibacterial agents administrable orally or by injection (see Examples 28 to 31 below).

The compounds of the invention can be administered orally or parenterally in an effective amount to a warm-blooded animal as a drug for treatment or prevention of bacterial infectious diseases.

When the compounds of this invention are used as antibacterial agents for human, it is recommended that they be administered in a dose of 5 mg to 5 g per day once or several times daily, although the dose may be varied depending upon the age, body weight and symptom of a patient, the administration route, etc. The compounds may be administered orally or parenterally.

The compounds of this invention may be administered in their as-obtained powder form, but they are usually administered in the form of a pharmaceutical preparation together with pharmaceutically acceptable adjuvants. Specific examples of the pharmaceutical preparations are tablets, solutions, capsules, granules, fine granules, pellets, powders, syrups, injections, and ointments. These pharmaceutical preparations are prepared by methods known per se. Adjuvants for oral administration are those which are commonly used in the field of formulating pharmaceutical preparations and do not react with the compounds of the invention, such as starch, mannitol, crystalline cellulose, CMC Na, water, ethanol, etc. Adjuvants for injections are those commonly used in the field of injection such as water, isotonic sodium chloride solution, glucose solution and transfusion solution.

The above liquid preparations and ointments can also be used for local treatments in oto-rhino-laryngology or ophthalmology.

The following examples illustrate the production of the compounds of this invention more specifically.

REFERENTIAL EXAMPLE 1

1-Cyclopropyl-5,6,7,8-tetrafluoro-1,4-dihydro4-oxoquinoline-3-carboxylic acid:

(1) A mixture of the known compound, ethyl pentafluorobenzoylacetate [J. Org. Chem., 35, 930 (1970)] (25 g), ethyl orthoformate (20 g), and acetic anhydride (23 g) was refluxed for 2 hours. The reaction mixture was evaporated to dryness under reduced pressure. The residue was dissolved in diethyl ether and allowed to react with cyclopropylamine (5.1 g) to give ethyl 2-pentafluorobenzoyl-3-cyclopropylaminoacrylate (28 g), m.p. 89° C.

(2) The above compound (28 g) was dissolved in dry tetrahydrofuran and allowed to react with 60% sodium hydride (3.85 g) at room temperature to give ethyl 1-cyclopropyl-5,6,7,8-tetrafluoro-1,4-dihydro-4-oxoquinoline-3-carboxylate (18.4 g), m.p. 170°–171° C.

(3) The above compound (10 g) was hydrolyzed by refluxing it in a mixture of glacial acetic acid (60 ml), water (500 ml) and concentrated sulfuric acid (7 ml) for 30 minutes to give 1-cyclopropyl-5,6,7,8-tetrafluoro-1,4-dihydro-4-oxoquinoline-3-carboxylic acid (8.7 g), 181°–182° C.

REFERENTIAL EXAMPLE 2

5-Amino-1-cyclopropyl-6,7,8-trifluoro-1,4-dihydro-4-oxoquinoline-3-carboxylic acid:

(1) A mixture of ethyl 1-cyclopropyl-5,6,7,8-tetrafluor-1,4-dihydro-4-oxoquinoline-3-carboxylate (28.2 g) prepared in Referential Example 1 (2), benzylamine (9.8 ml), anhydrous potassium carbonate (23.6 g), and acetonitrile (140 ml) was heated at 100°–110° C. for 1 hour to give ethyl 5-benzylamino-1-cyclopropyl-6,7,8-trifluoro-1,4-dihydro-4-oxoquinoline3-carboxylate (21.4 g), which was recrystallized from ethanol, m.p. 134°–135° C.

(2) The above compound (20 g) was dissolved in acetic acid (100 ml) and ethanol (150 ml), and hydrogenolyzed in the presence of 5% palladium-carbon (0.5 g) to give ethyl 5-amino-1-cyclopropyl-6,7,8-trifluoro-1,4 -dihydro-4-oxoquinoline-3-carboxylate (14.1 g), which was recrystallized from chloroform-ethanol, m.p. 236°–237° C.

(3) A mixture of the above compound (12.6 g), acetic acid (80 ml), water (50 ml), and concentrated sulfuric acid (9 ml) was heated at 100°–110 C. for 40 minutes to give 5-amino-1-cyclopropyl-6,7,8-trifluoro1,4-dihydro-4-oxoquinoline-3-carboxylic acid (11.1 g), which was recrystallized from chloroform-ethanol, m.p. 294°–295° C.

EXAMPLE 1

Cyclopropyl-5,6,8-trifluoro-7-(3-methyl-1-piperazinyl)-1,4-dihydro-4-oxoquinoline-3-carboxylic acid and its hydrochloride:

A mixture of 1-cyclopropyl-5,6,7,8-tetrafluoro-1,4-dihydro-4-oxoquinoline-3-carboxylic acid (910 mg), 2-methylpiperazine (320 mg, and pyridine (10 ml) was stirred at 80° C. for 1 hour. After evaporating the reaction mixture under reduced pressure, the residue was dissolved in dilute aqueous ammonia and treated with activated carbon. The filtrate was evaporated under reduced pressure and adjusted to pH 7–8. The resulting crystals were collected by filtration, washed with water, and dried to give 1-cyclopropyl-5,6,8-trifluoro-7-(3-methyl 1-piperazinyl)-1,4-dihydro-4-oxoquinoline-3-carboxylic acid (810 mg), m.p. 235°–237° C.

EXAMPLE 2

1-Cyclopropyl-5,6,8-trifluoro-7-(1-piperazinyl)-1,4-dihydro-4-oxoquinoline-3-carboxylic acid and its hydrochloride:

(1) A mixture of 1-cyclopropyl-5,6,7,8-tetrafluoro-1,4-dihydro-4-oxoquinoline-3-carboxylic acid (2.0 g), 4-formylpiperazine (0.75 g), and pyridine (30 ml) was stirred at 50° C. for 1 hour. The reaction mixture was concentrated to dryness under reduced pressure. The residue was mixed with water and extracted with chloroform. The extract was dried, and chloroform was evaporated. Ethanol was added to the residue, and the precipitated crystals were collected by filtration. Recrystallization from chloroform-ethanol gave 1-cyclopropyl-5,6,8-trifluoro-7-(4-formyl-1-piperazinyl)-1,4-dihydro-4-oxoquinoline-3-carboxylic acid (1.58 g), m.p. 290°–297° C.

(2) A mixture of the resulting carboxylic acid (0.5 g) and 15% hydrochloric acid (15 ml) was stirred at 90° to 100° C. for 1 hour. The reaction mixture was concentrated to dryness under reduced pressure. The resulting crystals were recrystallized from water to give 1-cyclopropyl-5,6,8-trifluoro-7-(1-piperazinyl)-1,4-dihydro-4-oxoquinoline-3-carboxylic acid hydrochloride (0.25 g), m.p. 270°–280° C. (decomp.).

(3) The resulting compound (170 mg) was dissolved in 5 ml of water, and adjusted to pH 7-8 with 10% aqueous ammonia. The precipitated crystals were collected by filtration, washed with water, and dried to give 1-cyclopropyl-5,6,8-trifluoro-7-(1-piperazinyl)-1,4-dihydro-4-oxoquinoline-3-carboxylic acid (140 mg), m.p. 208°–213° C.

EXAMPLE 3

1-Cyclopropyl-5,6,8-trifluoro-7-(cis-3,5-dimethyl-1-piperazinyl)-1,4-dihydro-4-oxoquinoline-3-carboxylic acid:

In the same manner as described in Example 1, a mixture of 1-cyclopropyl-5,6,7,8-tetrafluoro-1,4-dihydro-4-oxoquinoline-3-carboxylic acid, cis-2,6-dimethylpiperazine, and dimethylformamide was stirred at room temperature for 24 hours to give 1-cyclopropyl-5,6,8-trifluoro-7-(cis-3,5-dimethyl-1-piperazinyl)-1,4-dihydro-4-oxoquinoline-3-carboxylic acid, which was recrystallized from chloroform-ethanol, m.p. 259°–260° C.

EXAMPLE 4

1-Cyclopropyl-5,6,8-trifluoro-7-(3-fluoromethyl-1-piperazinyl)-1,4-dihydro-4-oxoquinoline-3-carboxylic acid:

In the same manner as described in Example 1, a mixture of 1-cyclopropyl-5,6,7,8-tetrafluoro-1,4-dihydro4-oxoquinoline-3-carboxylic acid, 2-fluoromethylpiperazine, and dioxane was refluxed for 5 hours to give 1-cyclopropyl-5,6,8-trifluoro-7-(3-fluoromethyl-1-piperazinyl)-1,4-dihydro-4-oxoquinoline-3-carboxylic acid, which was recrystallized from chloroform, m.p. 219°–220° C.

EXAMPLE 5

7-(3-Amino-3-methyl-1-pyrrolidinyl)-1-cyclopropyl-5,6,8-trifluoro-1,4-dihydro-4-oxoquinoline-3carboxylic acid:

A mixture of 1-cyclopropyl-5,6,7,8-tetrafluoro-1,4-dihydro-4-oxoquinoline-3-carboxylic acid (0.8 g), 3-amino-3-methylpyrrolidine (0.8 g), and acetonitrile (35 ml) was stirred at 50° C. for 30 minutes. The precipitated crystals were collected by filtration, and washed with water. The crystals were dissolved in 10% aqueous ammonia, treated with activated carbon, and concentrated under reduced pressure. The precipitated crystals were collected by filtration, washed with water and dried to give 7-(3-amino-3-methyl-1-pyrrolidinyl)-1-cyclopropyl-5,6,8-trifluoro-1,4-dihydro-4-oxoquinoline 3-carboxylic acid (0.81 g), m.p. 280°–282° C.

EXAMPLE 6

7-(cis-3-Amino-4-methyl-1-pyrrolidinyl)-1-cyclopropyl-5,6,8-trifluoro-1,4-dihydro-4-oxoquinoline3-carboxylic acid:

In the same manner as described in Example 5, a mixture of 1-cyclopropyl-5,6,7,8-tetrafluoro-1,4-dihydro-4-oxoquinoline-3-carboxylic acid, cis-3-amino-4-methylpyrrolidine, and pyridine was stirred at 50° C. for 30 minutes to give 7-(cis-3-amino-4-methyl-1-pyrrolidinyl)-1-cyclopropyl-5,6,8-trifluoro-1,4-dihydro-4-oxoquinoline-3-carboxylic acid, m.p. 264°–265° C.

EXAMPLE 7

7-(trans-3-Amino-4-methyl-1-pyrrolidinyl)-1-cyclopropyl-5,6,8-trifluoro-1,4-dihydro-4-oxoquinoline3-carboxylic acid:

In the same manner as described in Example 5, a mixture of 1-cyclopropyl-5,6,7,8-tetrafluoro-1,4-dihydro-4-oxoquinoline-3-carboxylic acid, trans-3-amino4-methylpyrrolidine, and xylene was refluxed for 3 hours to give 7-(trans-3-amino-4-methyl-1-pyrrolidinyl)-1-cyclopropyl-5,6,8-trifluoro-1,4-dihydro-4-oxoquinoline3-carboxylic acid, m.p. 255°–256° C.

EXAMPLE 8

7-(cis-3-Amino-4-fluoromethyl-1-pyrrolidinyl)1-cyclopropyl-5,6,8-trifluoro-1,4-dihydro-4-oxoquinoline3-carboxylic acid:

(1) A mixture of 1-cyclopropyl-5,6,7,8-tetrafluoro-1,4-dihydro-4-oxoquinoline-3-carboxylic acid (1.32 g), cis-3-trifluoroacetylamino-4-fluoromethylpyrrolidine (1.41 g), and pyridine (10 ml) was refluxed for 5 hours. The reaction mixture was concentrated to dryness under reduced pressure. Water was added to the residue, and the resulting precipitate were collected. Recrystallization from dimethylformamide gave 1-cyclopropyl-5,6,8-trifluoro-7-(cis-3-trifluoroacetylamino-4-fluoromethyl-1-pyrrolidinyl)-1,4-dihydro-4-oxoquinoline-3-carboxylic acid (1.25 g), m.p. 283°–284° C.

(2) A mixture of the resulting compound (1.0 g) and a 10% aqueous solution of sodium hydroxide (5 ml) was stirred at 80° to 90° C. for 1 hour. The reaction mixture was adjusted to pH 8–9 with glacial acetic acid, and the precipitated crystals were collected by filtration. Recrystallization from dimethylformamide gave 7-(cis3-amino-4-fluoromethyl-1-pyrrolidinyl)-1-cyclopropyl-5,6,8-trifluoro-1,4-dihydro-4-oxoquinoline-3-carboxylic acid (0.52 g), m.p. 252°–253° C.

EXAMPLE 9

7-(trans-3-Amino-4-fluoromethyl-3-methyl-1-pyrrolidinyl)-1-cyclopropyl-5,6,8-trifluoro-1,4-dihydro4-oxoquinoline-3-carboxylic acid:

In the same manner as described in Example 5, a mixture of 1-cyclopropyl-5,6,7,8-tetrafluoro-1,4-dihydro-4-oxoquinoline-3-carboxylic acid, trans-3-amino-4-fluoromethyl-3-methylpyrrolidine, and dimethyl sulfoxide was stirred at 150° C. for 2 hours to give 7-(trans-3-amino-4-fluoromethyl-3-methyl-1-pyrrolidinyl)-1-cyclopropyl-5,6,8-trifluoro-1,4-dihydro-4-oxoquinoline-3-carboxylic acid, which was recrystallized from chloroform-ethanol, m.p. >300° C.

EXAMPLE 10

5-Amino-7-(3-amino-3-methyl-1-pyrrolidinyl)1-cyclopropyl-6,8-difluoro-1,4-dihydro-4-oxoquinoline3-carboxylic acid and its salts:

(1) A mixture of 5-amino-1-cyclopropyl-6,7,8-trifluoro-1,4-dihydro-4-oxoquinoline-3-carboxylic acid (1.5 g), 3-amino-3-methylpyrrolidine (0.76 g), DBU (0.77 g), and acetonitrile (30 ml) was refluxed for 7 hours. The precipitated crystals were collected by filtration after cooling, and washed with acetonitrile. The crystals were suspended in water (50 ml) and dissolved by addition of a 10% aqueous solution of acetic acid. The solution was treated with activated carbon, and adjusted to pH 7–8 with 10% aqueous ammonia. The precipitated crystals were collected by filtration, washed with water and then with ethanol, and dried to give 5-amino-7-(3-amino-3-methyl1-pyrrolidinyl)-1-cyclopropyl-6,8-difluoro-1,4-dihydro4-oxoquinoline-3-carboxylic acid (1.15 g), m.p. 271°–273° C. (decomp.).

(2) The resulting compound (200 mg) was dissolved in 20% hydrochloric acid (5 ml), and the solution was concentrated to dryness under reduced pressure. Ethanol was added to the residue, and the resulting crystals were collected by filtration. Recrystallization from water ethanol gave 5-amino-7-(3-amino-3-methyl-1-pyrrolidinyl)1-cyclopropyl-6,8-difluoro-1,4-dihydro-4-oxoquinoline-3-carboxylic acid hydrochloride (145 mg), m.p. 293°–297° C. (decomp.).

(3) In the customary manner, acetic acid salt [m.p. 272°–274° C. (decomp.)] and methane sulfonic acid salt (m.p. >300 ° C.) were obtained.

EXAMPLE 11

5-Amino-7-(3-amino-3-ethyl-1-pyrrolidinyl)1-cyclopropyl-6,8-difluoro-1,4-dihydro-4-oxoquinoline-3-carboxylic acid:

In the same manner as described in Example 10 except using 3-amino-3-ethyl pyrrolidine in place of 3-amino-3-methylpyrrolidine, 5-amino-7-(3-amino-3-ethyl-1-pyrrolidinyl)-1-cyclopropyl-6,8-difluoro-1,4-dihydro-4-oxoquinoline-3-carboxylic acid was obtained, which is recrystallized from acetonitrile-chloroform, m.p. 205°–206° C.

EXAMPLE 12

5-Amino-7-(trans-3-amino-4-methyl-1-pyrrolidinyl)-1-cyclopropyl-6,8-difluoro-1,4-dihydro-4-oxoquinoline-3-carboxylic acid:

A mixture of 5-amino-1-cyclopropyl-6,7,8-trifluoro-1,4-dihydro-4-oxoquinoline-3-carboxylic acid (1.5 g), trans-3-amino-4-methylpyrrolidine (0.76 g), DBU (0.77 g), and acetonitrile (30 ml) was refluxed for 7 hours. The precipitated crystals were collected by filtration after cooling, washed with acetonitrile, and dried. Recrystallization from chloroform-ethanol gave cyclopropyl-6,8-difluoro-1,4-dihydro-4-oxoquinoline-3-cyclopropyl-6,8-difluoro-1,4-dihydro-4-oxoquinoline-3-carboxylic acid (1.05 g), m.p. 234°–236° C.

EXAMPLE 13

5-Amino-7-(trans-3-amino-4-ethyl-1-pyrrolidinyl)-1-cyclopropyl-6,8-difluoro-1,4-dihydro-4-oxoquinoline-3-carboxylic acid:

(1) A mixture of 5-amino-1-cyclopropyl-6,7,8-trifluoro-1,4-dihydro-4-oxoquinoline-3-carboxylic acid (1.36 g), trans-3-methoxycarbonylamino-4-ethyl pyrrolidine (0.94 g), diisopropylethylamine (0.88 g), and acetonitrile (20 ml) was refluxed for 15 hours. The precipitated crystals wee collected by filtration, and dried to give 5-amino-1-cyclopropyl-7-(trans-3-methoxycarbonylamino-4-ethyl-1-pyrrolidinyl)-6,8-difluoro-1,4-dihydro-4-oxoquinoline-3-carboxylic acid (1.15 g), recrystallized from chloroform-ethanol, m.p. 231°–232° C.

(2) A mixture of the above carboxylic acid (750 mg), 20% aqueous potassium hydroxide (2 ml) and methanol (4 ml) was refluxed for 10 hours, and concentrated under reduced pressure. The residue was diluted with water, and adjusted to pH 8 with acetic acid. After cooling, the precipitated crystals were collected by filtration, washed successively with water and ethanol, and then dried to give 5-amino-1-cyclopropyl-7-(trans-3-amino4-ethyl-1-pyrrolidinyl)-6,8-difluoro-1,4-dihydro-4-oxoquinoline-3-carboxylic acid (610 mg), m.p. 195°–196° C.

EXAMPLE 14

5-Amino-7-(cis-3-amino-4-fluoromethyl-1-pyrrolidinyl)-1-cyclopropyl-6,8-difluoro-1,4-dihydro-4-oxoquinoline-3-carboxylic acid:

(1) In the same manner as described in Example 13 (1), a mixture of 5-amino-1-cyclopropyl-6,7,8-trifluoro1,4-dihydro-4-oxoquinoline-3-carboxylic acid, cis-3-trifluoroacetylamino-4-fluoromethylpyrrolidine, diisopropylethylamine, and dioxane was refluxed for 12 hours to give 5-amino-7-(cis-3-trifluoroacetylamino4-fluoromethyl-1-pyrrolidinyl)-1-cyclopropyl-6,8-difluoro-1,4-dihydro-4-oxoquinoline-3-carboxylic acid.

(2) A mixture of the above carboxylic acid (1.0 g) and 10% aqueous sodium hydroxide (5 ml) was heated on a boiling water bath for 1 hour. The mixture was acidified with 10% aqueous acetic acid and then made weakly alkaline with concentrated aqueous ammonia. It was concentrated under reduced pressure, and the precipitated crystals were collected by filtration, washed with water and dried. Recrystallization from dimethylformamide gave 5-amino-1-cyclopropyl-7-(cis-3-amino-4- fluoromethyl-1-pyrrolidinyl)-6,8-difluoro-1,4-dihydro-4-oxoquinoline-3-carboxylic acid (615 mg), m.p. 248°–249° C.

EXAMPLE 15

5-Amino-7-(trans-3-amino-4-fluoromethyl-3-methyl-1-pyrrolidinyl)-1-cyclopropyl-6,8-difluoro-1,4-dihydro-4-oxoquinoline-3-carboxylic acid:

In the same manner as described in Example 13 (1), a mixture of 5-amino-1-cyclopropyl-6,7,8-trifluoro1,4-dihydro-4-oxoquinoline-3-carboxylic acid, trans-3-amino-4-fluoromethyl-3-methylpyrrolidine, triethylamine, and pyridine was refluxed for 1.5 hours to give 5-amino7-(trans-3-amino-4-fluoromethyl-3-methyl-1-pyrrolidinyl)1-cyclopropyl-6,8-difluoro-1,4-dihydro-4-oxoquinoline-3-carboxylic acid, which was recrystalized from chloroformethanol, m.p. 299°–301° C.

EXAMPLE 16

5-Amino-7-(cis-3-aminomethyl-4-methyl-1-pyrrolidinyl)-1-cyclopropyl-6,8-difluoro-1,4-dihydro-4-oxoquinoline-3-carboxylic acid and its hydrochloride:

(1) A mixture of 5-amino-1-cyclopropyl-6,7,8-trifluoro-1,4-dihydro-4-oxoquinoline-3-carboxylic acid (1.22 g), cis-3-aminomethyl-4-methylpyrrolidine (1.68 g), and acetonitrile (30 ml) was refluxed for 4.5 hours. The reaction mixture was concentrated to dryness under reduced pressure. The resulting crude crystals were recrystallized from ethanol to give 5-amino-7-(cis-3-aminomethyl-4-methyl-1-pyrrolidinyl)-1-cyclopropyl-6,8-difluoro-1,4-dihydro-4-oxoquinoline-3-carboxylic acid (1.3 g), recrystallized from ethanol-chloroform, m.p. 221°–223° C.

(2) The resulting compound (0.5 g) was suspended in ethanol, and concentrated hydrochloric acid (2 ml) was added. The mixture was stirred. The resulting crystals were collected by filtration, washed with ethanol, and dried. Recrystallization from water-ethanol gave 5-amino-7-(cis-3-aminomethyl-4-methyl-1-pyrrolidinyl)-1-cyclopropyl-6,8-difluoro-1,4-dihydro-4-oxoquinoline-3-carboxylic acid hydrochloride (0.59 g), m.p. 268°–271° C. (decomp.).

EXAMPLE 17

5-Amino-7-(trans-3-aminomethyl-4-methyl-1-pyrrolidinyl)-1-cyclopropyl-6,8-difluoro-1,4-dihydro4-oxoquinoline-3-carboxylic acid:

In the same manner as described in Example 16 (1), a mixture of 5-amino-1-cyclopropyl-6,7,8-trifluoro-1,4-dihydro-4-oxoquinoline-3-carboxylic acid, trans-3-aminomethyl-4-methylpyrrolidine, and dimethylformamide was stirred at room temperature for 24 hours to give 5-amino-7-(trans-3-aminomethyl-4-methyl-1-pyrrolidinyl)-1-cyclopropyl-6,8-difluoro-1,4-dihydro4-oxoquinoline-3-carboxylic acid, which was recrystalized from ethanol, m.p. 223°–225° C.

EXAMPLE 18

5-Amino-7-(trans-3-aminomethyl-4-ethyl-1-pyrrolidinyl)-1-cyclopropyl-6,8-difluoro-1,4-dihydro-4-oxoquinoline-3-carboxylic acid and its hydrochloride:

(1) A mixture of 5-amino-1-cyclopropyl-6,7,8-trifluoro-1,4-dihydro-4-oxoquinoline-3-carboxylic acid (1.57 g), trans-3-aminomethyl-4-ethyl pyrrolidine (0.88 g), DBU (0.8 g), and acetonitrile (30 ml) was refluxed for 4 hours. The precipitated crystals were collected by filtration after cooling. The crystals were suspended in ethanol, and concentrated hydrochloric acid (5 ml) was added, and the mixture was stirred. The precipitated crystals were collected by filtration, and recrystallized from water-ethanol to give 5-amino-7-(trans-3-aminomethyl-4-ethyl-1-pyrrolidinyl)-1-cyclopropyl-6,8-difluoro- 1,4-dihydro-4-oxoquinoline-3-carboxylic acid hydrochloride (1.01 g), m.p. 183°–184° C.

(2) This compound (300 mg) was suspended in water (20 ml), and the suspension was adjusted to pH 8 with 10% aqueous ammonia. It was extracted with chloroform, and the extract was dried and concentrated. The residue was recrystallized from ethanol to give 5-amino-7-(trans-3-aminomethyl-4-ethyl-1-pyrrolidinyl)-1-cyclopropyl-6,8-difluoro-1,4-dihydro-4-oxoquinoline-3-carboxylic acid (215 mg), m.p, 121°–122° C.

EXAMPLE 19

5-Amino-7-(cis-3-aminomethyl-4-ethyl-1-pyrrolidinyl)-1-cyclopropyl-6,8-difluoro-1,4-dihydro4-oxoquinoline-3-carboxylic acid:

(1) In the same manner as described in Example 18 (1), a mixture of 5-amino-1-cyclopropyl-6,7,8-trifluoro-1,4-dihydro-4-oxoquinoline-3-carboxylic acid, cis-3-aminomethyl-4-ethyl pyrrolidine, DBU, and xylene was refluxed for 3 hours to give 5-amino-7-(cis-3-aminomethyl-4-ethyl-1-pyrrolidinyl)-1-cyclopropyl-6,8-difluoro-1,4-dihydro-4-oxoquinoline-3-carboxylic acid hydrochloride, m.p. 252°–256° C. (decomp.).

(2) The above compound (200 mg) was suspended in water (20 ml), and adjusted to pH 8 with 10% aqueous ammonia. The crystals were collected by filtration, and recrystallized from ethanol-chloroform to give 5-amino-7-(cis-3-aminomethyl-4-ethyl-1-pyrrolidinyl)-1-cyclopropyl-6,8-difluoro-1,4-dihydro-4-oxoquinoline-3-carboxylic acid (114 mg), m.p. 220°–222° C. (decomp.).

EXAMPLE 20

5-Amino-7(cis-3-ethyl aminomethyl-4-ethyl-1-pyrrolidinyl)-1-cyclopropyl-6,8-difluoro-1,4-dihydro-4-oxoquinoline-3-carboxylic acid:

(1) In the same manner as described in Example 13 (1) except using cis-3-trifluoroacetylethylaminomethyl-4-ethyl pyrrolidine in place of trans-3-methoxycarbonylamino- 4-ethyl pyrrolidine, 5-amino-7-(cis-3-trifluoroacetylethylaminomethyl-4-ethyl-1-pyrrolidinyl)-1-cyclopropyl-6,8-difluoro-1,4-dihydro-4-oxoquinoline-3-carboxylic acid was obtained, which was recrystalized from ethyl acetate-n-hexane, m.p. 145°–146° C.

(2) In the same manner as described in Example 14 (2), a mixture of the above compound, 5% aqueous sodium hydroxide, and ethanol was heated on a boiling-water bath for 15 minutes to give 5-amino-7-(cis-3-ethyl aminomethyl-4-ethyl-1-pyrrolidinyl)-1-cyclopropyl-6,8-difluoro-1,4-dihydro-4-oxoquinoline-3-carboxylic acid, m.p. 171°–172° C.

EXAMPLE 21

5-Amino-7-(3-amino-3-methyl-1-pyrrolidinyl)1-cyclopropyl-6,8-difluoro-1,4-dihydro-4-oxoquinoline3-carboxylic acid:

A mixture of 7-(3-amino-3-methyl-1-pyrrolidinyl)-1-cyclopropyl-5,6,8-trifluoro-1,4-dihydro-4-oxoquinoline-3-carboxylic acid (150 mg) and 28% aqueous ammonia (15 ml) was heated at 100° C. for 48 hours in a sealed tube. The reaction mixture was evaporated to dryness under reduced pressure and water was added to the residue. The resulting crystals were treated in the same manner as described in Example 10 (1) to give 5-amino7-(3-amino-3-methyl-1-pyrrolidinyl)-1-cyclopropyl-6,8-difluoro-1,4-dihydro-4-oxoquinoline-3-carboxylic acid (93 mg), m.p. 271°–273° C (decomp.).

Referential Example 3

5-Benzylamino-7-(trans-3-amino-4-methyl-1-pyrrolidinyl)-1-cyclopropyl-6,8-difluoro-1,4-dihydro-4-oxoquinoline-3-carboxylic acid:

A mixture of 7-(trans-3-amino-4-methyl-1-pyrrolidinyl)-1-cyclopropyl-5,6,8-trifluoro-1,4-dihydro-4-oxoquinoline-3-carboxylic acid (1.0 g), benzylamine (420 mg), and pyridine (5 ml) was heated at 100°–110° C. for 3 hours. The reaction mixture was evaporated to dryness under reduced pressure. After addition of water to the residue, the mixture was acidified with 10% aqueous acetic acid and extracted with chloroform. The extract was dried and evaporated. The resulting crystals were recrystallized from ethanol-ether to give 5-benzylamino-(7-trans-3-amino-4-methyl-1-pyrrolidinyl)-1-cyclopropyl-6,8-difluoro-1,4-dihydro-4-oxoquinoline-3-carboxylic acid (730 mg).

EXAMPLE 22

5-Amino-(7-trans-3-amino-4-methyl-1-pyrrolidinyl)-1-cyclopropyl-6,8-difluoro-1,4-dihydro-4-oxoquinoline-3-carboxylic acid:

A mixture of 5-benzylamino-(7-trans-3-amino-4-methyl-1-pyrrolidinyl)-1-cyclopropyl-6,8-difluoro-1,4-dihydro-4-oxoquinoline-3-carboxylic acid (700 mg), 5% palladium-carbon (0.2 g), acetic acid (10 ml), and ethanol (15 ml) was stirred at room temperature for 30 minutes under a hydrogen stream. The catalyst was filtered off and the filtrate was evaporated under reduced pressure. After addition of water to the residue, the mixture was adjusted to pH 8 with aqueous ammonia. The resulting crystals were filtered to give 5-amino7-(trans-3-amino-4-methyl-1-pyrrolidinyl)-1-cyclopropyl6,8-difluoro-1,4-dihydro-4-oxoquinoline-3-carboxylic acid (510 mg), m.p. 234°–236° C.

Referential Example 4

Ethyl 7-(3-acetylamino-3-methyl-1-pyrrolidinyl)-1-cyclopropyl-5-ethoxycarbonylamino-6,8-difluoro1,4-dihydro-4-oxoquinoline-3-carboxylate:

In the same manner as described in Example 2 (1), ethyl 1-cyclopropyl-5-ethoxycarbonylamino-6,7,8-trifluoro1,4-dihydro-4-oxoquinoline-3-carboxylate was allowed to react with 3-acetylamino-3-methylpyrrolidine to give ethyl 7-(3-acetylamino-3-methyl-1-pyrrolidinyl)-1-cyclopropyl5-ethoxycarbonylamino-6,8-difluoro-1,4-dihydro-4-oxoquinoline-3-carboxylate.

EXAMPLE 23

5-Amino-7-(3-amino-3-methyl-1-pyrroldinyl)-1-cyclopropyl-6,8-difluoro-1,4-dihydro-4-oxoquinoline-3-carboxylic acid hydrochloride:

A mixture of ethyl 7-(3-acetylamino-3-methyl1-pyrroldinyl)-1-cyclopropyl-5-ethoxycarbonylamino-6,8-difluoro-1,4-dihydro-4-oxoquinoline-3-carboxylate, 20% aqueous sodium hydroxide, and ethanol was refluxed for 12 hours. The reaction mixture was treated with activated carbon and adjusted at pH 1–2 with 10% hydrochloric acid. After cooling, the resulting crystals were collected by filtration and recrystallized from water-ethanol to give 5-amino-7-(3-amino-3-methyl-1-pyrroldinyl)-1-cyclopropyl6,8-difluoro-1,4-dihydro-4-oxoquinoline-3-carboxylic acid hydrochloride, m.p. 293°–297° C. (decomp.).

REFERENTIAL EXAMPLE 5

Ethyl 2-4-(4-acetyl-3-methyl-1-piperazinyl)2,3,5,6-tetrafluorobenzoyl]-3-cyclopropylaminoacrylate:

(1) Ethyl pentafluorobenzoylacetate was allowed to react with 2-methylpiperazine and the reaction product was then acetylated to give ethyl 4-(acetyl-3-methyl1-piperazinyl)-2,3,5,6-tetrafluorobenzoylacetate.

(2) The above compound was treated in the same manner as described in Referential Example 1 (1) to give ethyl 2-[4-(4-acetyl-3-methyl-1-piperazinyl)-2,3,5,6-tetrafluorobenzoyl)-3-cyclopropylaminoacrylate.

EXAMPLE 24

1-Cyclopropyl-5,6,8-trifluoro-7-(3-methyl-1-piperazinyl)-1,4-dihydro-4-oxoquinoline-3-carboxylic acid:

(1) Ethyl-2-4-(4-acetyl-3-methyl-1-piperazinyl)2,3,5,6-tetrafluorobenzoyl]-3-cyclopropylaminoacrylate (2.0 g) was dissolved in dry tetrahydrofuran (10 ml) and 60% sodium hydride (200 mg) was added. The mixture was stirred at room temperature for 10 minutes. After evaporating the reaction mixture under reduced pressure, water was added to the residue and the mixture was extracted with chloroform. The extract was evaporated to give ethyl 7-(3-acetyl-3-methyl-1-piperazinyl)-1-cyclopropyl-5,6,8-trifluoro-1,4-dihydro-4-oxoquinoline-3-carboxylate (1.34 g).

(2) A mixture of the above compound (1.2 g) and 20% hydrochloric acid (20 ml) was refluxed for 10 hours. After evaporating the reaction mixture under reduced pressure, the residue was dissolved in water (20 ml). The solution was adjusted to pH 7–8 with 10% aqueous ammonia. The resulting crystals were filtered to give 1-cyclopropyl-5,6,8-trifluoro-7-(3-methyl-1-piperazinyl)1,4-dihydro-4-oxoquinoline-3-carboxylic acid (0.96 g), m.p. 235°–237° C.

Examples 25 to 27 illustrate pharmaceutical compositions containing the compounds of the invention as active ingredients.

EXAMPLE 25

| | |
|---|---|
| Compound of this invention | 250 g |
| Starch | 50 g |
| Lactose | 35 g |
| Talc | 15 g |

The above components were blended with ethanol and granulated and filled into 1,000 capsules in accordance with conventional methods.

EXAMPLE 26

| | |
|---|---|
| Compound of this invention | 250 g |
| Starch | 54 g |
| Calcium carboxymethyl cellulose | 40 g |
| Microcrystalline cellulose | 50 g |
| Magnesium stearate | 6 g |

The above components were blended with ethanol and granulated and made into tablets in a manner known per se. Thus, 1,000 tablets each weighing 400 mg were formed.

EXAMPLE 27

| Compound of this invention | 50 g |
|---|---|
| Lactic acid | 120 g |

The above components were dissolved in distilled water sufficient to make ten liters solution. The solution was adjusted to pH about 4 with an aqueous sodium hydroxide solution, and then filled in ampules (10 ml) to make an injectable solution.

The chemotherapeutic activities of the compounds of this invention are shown in Examples 28–31 hereinbelow. The compounds tested comprise:

Compound 1: 1-cyclopropyl-5,6,8-trifluoro-7-(3-methyl-1-piperazinyl)-1,4-dihydro-4-oxoquinoline-3-carboxylic acid, Compound 2: 1-cyclopropyl-5,6,8-trifluoro-7-(cis3-amino-4-methyl-1-pyrrolidinyl)-1,4-dihydro-4-oxoquinoline-3-carboxylic acid, Compound 3: 5-amino-7-(3-amino-3-methyl-1-pyrrolidinyl)-1-cyclopropyl-6,8-difluoro-1,4-dihydro-4-oxoquinoline-3-carboxylic acid, Compound 4: 5-amino-7-(3-amino-3-ethyl-1-pyrrolidinyl)-1-cyclopropyl-6,8-difluoro-1,4-dihydro-4-oxoquinoline-3-carboxylic acid, Compound 5: 5-amino-7-(trans-3-amino-4-methyl-1-pyrrolidinyl)-1-cyclopropyl-6,8-difluoro-1,4-dihydro-4-oxoquinoline-3-carboxylic acid, Compound 6: 5-amino-7-(cis-3-aminomethyl-4-methyl-1-pyrrolidinyl)-1-cyclopropyl-6,8-difluoro-1,4-dihydro-4-oxoquinoline-3-carboxylic acid hydrochloride, Compound A: 5-amino-1-ethyl-6,8-difluoro-7-(1piperazinyl)-1,4-dihydro-4-oxoquinoline-3-carboxylic acid.

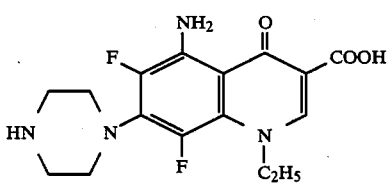

Compound B: 1-cyclopropyl-6-fluoro-7-(1-piperazinyl)-1,4-dihydro-4-oxoquinoline-3carboxylic acid hydrochloride

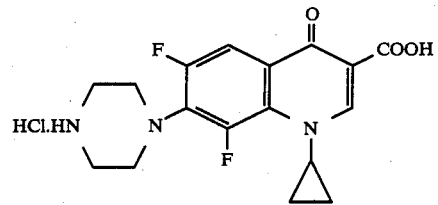

EXAMPLE 28

The antibacterial activity in vitro is shown in Table 1. The numbers in the table show minimum inhibitory concentrations (MIC) (μg/ml), calculated for free base. The minimum inhibitory concentration was determined by the twofold agar-dilution method, which was recommended by Japan Society of Chemotherapy (Chemotherapy, 29(1), (1981)), using Muller-Hinton agar. One loopful of an overnight culture of test organisms in Mueller-Hinton broth was inoculated onto 10-ml drug-containing agar layers in petri dishes. Bacterial inocula contained approximately $10^6$ colonyl-forming units. Bacterial growth was observed after 20-hour incubation at 37° C. The MIC was defined as the lowest drug concentration which prevented visible bacterial growth.

TABLE 1

In vitro antibacterial activity

| Strains | Compounds | | | | | | | |
|---|---|---|---|---|---|---|---|---|
| | 1 | 2 | 3 | 4 | 5 | 6 | A | B |
| Gram-negative | | | | | | | | |
| S. aureus 209P JC-1 | 0.2 | 0.05 | 0.025 | 0.025 | 0.025 | <0.0031 | 0.2 | 0.1 |
| S. aureus No. 50774 | 0.2 | 0.05 | 0.025 | 0.025 | 0.0125 | 0.0031 | 0.2 | 0.1 |
| S. aureus No. 80 | 0.2 | 0.05 | 0.0063 | 0.0063 | 0.0125 | 0.0031 | 0.2 | 0.39 |
| S. pyogenes A 65 | 1.56 | 0.39 | 0.1 | 0.2 | 0.1 | 0.0125 | 12.5 | 0.2 |
| S. pyogenes Cook | 1.56 | 0.2 | 0.1 | 0.1 | 0.1 | 0.0063 | 6.25 | 0.2 |
| Gram-positive | | | | | | | | |
| E. coli P-51213 | 0.1 | 0.05 | 0.05 | 0.05 | 0.025 | 0.0125 | 0.39 | 0.05 |
| P. aeruginosa 12 | 0.78 | 0.39 | 0.2 | 0.2 | 0.1 | 0.1 | 0.78 | 0.1 |
| M. bovis P-7101 | 1.56 | 0.39 | 0.2 | 0.2 | 0.1 | 0.2 | 3.13 | 1.56 |
| M. lacunata P-7102 | 6.25 | 0.78 | 0.78 | 0.78 | 0.39 | 0.2 | 6.25 | 6.25 |
| Flavobacterium sp P-7201 | 0.39 | 0.2 | 0.1 | 0.05 | 0.05 | 0.025 | 0.78 | 0.39 |
| B. abortus kusayanagi | 3.13 | 0.78 | 0.39 | 0.39 | 0.2 | 0.39 | 3.13 | 1.56 |

The following can be seen from the results shown in Table 1.

(1) Compounds 1, 2, 3, 4 and 5 of this invention exhibit very high antibacterial activities against Gram-positive and Gram-negative bacteria.

(2) Compounds of this invention exhibit better in vitro antibacterial activity against Gram-positive and Gram-negative bacteria than Compound A.

EXAMPLE 29

In vivo efficacy against systemic infections in mice is shown in Table 2.

Compounds were each dissolved in deionized water. Each of the solutions was orally administered to mice infected with each of the test organisms under the conditions shown hereinbelow, and the median effective dose (ED 50) was calculated by prohibit analysis. The numerals in the table show $ED_{50}$ (mg/kg) value, calculated for free base.

Experimental conditions:

Mice: Male mice (ddY-S) weighing about 20 g Infection:

Staphylococcus aureus 50774

Intravenous infection with $5 \times 10^8$ cells per mouse suspended in saline.

Streptococcus pyogenes A65
 Intraperitoneal infection with $3 \times 10^7$ cells per mouse suspended in brain heart infusion broth.

Pseudomonas aeruginosa 12
 Intraperitoneal infection with about $5 \times 10^3$ cells per mouse suspended in tryptosoy broth with 4% mucin.

Medication

Twice, immediately and 6 hours after infection.

Observation

For 14 days in case of Staphylococcus aureus 50774.
For 7 days in case of other organisms.

TABLE 2

In vivo efficacy against systemic infections in mice

| Strains | Compounds | | | |
|---|---|---|---|---|
| | 1 | 3 | A | B |
| S. aureus 50774 | 2.40 | — | — | =11.7 |
| S. pyogenes A65 | 17.3 | 9.14 | >25 | 23.9 |
| P. aeruginosa 12 | 2.46 | 1.68 | 15.0 | 2.78 |

The following conclusions can be drawn from the results shown in Table 2.

(1) Compounds 1 and 3 of this invention show potent therapeutic effects on systemic infections by Gram-positive and Gram-negative bacteria.

(2) Compounds 1 and 3 of this invention exhibit better therapeutic effects against systemic infections by Gram-positive and Gram-negative bacteria than Compounds A and B.

(3) Particularly, Compounds 1 and 3 show a better efficacy against systemic infection by *P. aeruginosa* 12 than Compound A, and Compound 1 shows a better efficacy against systemic infection by *S. aureus* 50774 than Compound B.

Example 30 (Acute toxicity)

A solution containing each of compounds of this invention in various concentrations was orally given to male mice (ddY) at a dose of 0.1 ml per 10 g of body weight. The number of dead mice was counted after 7 days, and the value of median lethal dose ($LD_{50}$ mg/kg) was calculated in accordance with the Behrens-Kaerber method. The results are shown in Table 3.

TABLE 3

Acute oral toxicity in mice

| Compound | $LD_{50}$ (mg/kg) |
|---|---|
| 1 | >2000 |
| 2 | >2000 |
| 3 | >2000 |
| 4 | >2000 |
| 5 | >2000 |

From the results shown in Table 3 it is seen that the compounds 1, 2, 3, 4 and 5 of this invention have low oral toxicity.

EXAMPLE 31

A solution of Compound 1 dissolved in saline with an equimolar amount of sodium hydroxide or a solution of Compound B in saline was administered orally or intravenously to male mice (ddY) weighing about 30 g to a dose of 5 mg/kg. Urine and feces were collected in metabolism cages over a period of 24 hours. The concentration of the compounds in these samples was determined by thin-layer cup-plate method using *Escherichia coli* Kp as an indicator organism.

TABLE 4

| Compound | Urinary and fecal excretion in mice | | | | |
|---|---|---|---|---|---|
| | Route | Item | Urine | Feces | Total |
| 1 | iv | c | 24.3 | 101 | |
| | | r | 63.6 | 14.0 | 77.6 |
| | po | c | 34.3 | 144 | |
| | | r | 63.4 | 22.3 | 85.7 |
| B | iv | c | 24.3 | 138 | |
| | | r | 35.4 | 8.96 | 44.4 |
| | po | c | 4.05 | 341 | |
| | | r | 6.39 | 26.3 | 32.7 | c: concentration (g/ml)
r: recovery (%)

The following can be seen from the results shown in Table 4.

(1) High total recovery of Compound 1 of this invention shows good metabolic stability.

2) The urinary excretion of Compound 1 of this invention is very good. It shows that Compound 1 has very good oral absorbability.

(3) The urinary level (34.3 g/ml) of Compound 1 amounts to about 22 to 2700 times the MIC values (0.0125 to 1.56 g/ml) against various bacteria as shown in Table 1.

(4) Compound 1 of this invention is superior to Compound B in metabolic stability and oral absorbability.

As shown in Tables 1 to 4, the compounds of this invention exhibit a superior therapeutic effect on the experimental infections with Gram-positive and Gram-negative bacteria with low toxicity. They also have good absorbability and good metabolic stability. Moreover they have low cytotoxicity and when administered parenterally, show low local irritation. Accordingly, these compounds are useful as antibacterial agents administerable orally or by injection.

What is claimed is:

1. A quinoline derivative of the formula wherein
Z is an amino group or a halogen atom,
R is in which R₃ is a lower alkyl or haloalkyl group,
R₄ is a hydrogen atom or a lower alkyl group, and
R₅ and R₆ are the same or different and each represents
a hydrogen atom or a lower alkyl group, or a pharmaceutically acceptable ester thereof or a pharmaceutically acceptable salt of said derivative or ester.

2. A compound as claimed in claim 1, wherein Z is a halogen atom.

3. A compound as claimed in claim 1, wherein Z is an amino group.

4. A lower alkyl ester of a quinoline derivative of the formula

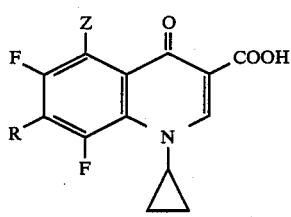

wherein Z and R are as defined in claim 1, or a salt thereof.

5. 1-Cyclopropyl-5,6,8-trifluoro-7-(3-amino-4-methyl-1-pyrrolidinyl)-1,4-dihydro-4-oxoquinoline-3-carboxylic acid or a pharmaceutically acceptable acid addition salt thereof.

6. 5-Amino-7-(3-amino-3-methyl-1-pyrrolidinyl)1-cyclopropyl-6,8-difluoro-1,4-dihydro-4-oxoquinoline-3-carboxylic acid or a pharmaceutically acceptable acid addition salt thereof.

7. 5-Amino-7-(3-amino-3-ethyl-1-pyrrolidinyl)-1-cyclopropyl-6,8-difluoro-1,4-dihydro-4-oxoquinoline-3-carboxylic acid or a pharmaceutically acceptable acid addition salt thereof.

8. 5-Amino-7-(3-amino-4-methyl-1-pyrrolidinyl)-1-cyclopropyl-6,8-difluoro-1,4-dihydro-4-oxoquinoline-3-carboxylic acid or a pharmaceutically acceptable acid addition salt thereof.

9. A pharmaceutically composition comprising a compound defined in claim 1 as an active ingredient and a pharmaceutically acceptable carrier.

10. A method for treatment of a bacterial infectious disease which comprises administering an effective amount of a compound defined in claim 1 to a warm-blooded animal.

* * * * *

UNITED STATES PATENT AND TRADEMARK OFFICE
CERTIFICATE OF CORRECTION

PATENT NO. : 4,886,810

DATED : December 12, 1989

INVENTOR(S) : JUN-ICHI MATSUMOTO, TERUYUKI MIYAMOTO, HIROSHI EGAWA and SHINICHI NAKAMURA It is certified that error appears in the above-identified patent and that said Letters Patent is hereby corrected as shown below:

Column 13, line 10, before "Cyclopropyl" insert —1- —;

line 12, delete "and its hydrochloride";

line 32, change "4-formylpiperazine" to read —1-formylpiperazine—.

Column 18, line 19, after "acid" insert —and its hydrochloride—.

Column 19, line 18, change "(7-trans" to —7-(trans—;

Column 19, line 23, change "5-Amino-(7-trans" to read —5-Amino-7-(trans —;

line 26, change "5-benzylamino-(7-trans" to read —5-benzylamino-7-(trans—;

line 66, change "cyclopropyl6,8-" to read —cyclopropyl-6,8- —.

Column 20, line 20, change "Ethyl-2-4-" to read —Ethyl 2-[4- —;

line 28, change "3-acetyl" to read —4-acetyl—.

UNITED STATES PATENT AND TRADEMARK OFFICE
CERTIFICATE OF CORRECTION

PATENT NO.   : 4,886,810

DATED        : December 12, 1989

INVENTOR(S)  : JUN-ICHI MATSUMOTO, TERUYUKI MIYAMOTO, HIROSHI EGAWA and SHINICHI NAKAMURA It is certified that error appears in the above-identified patent and that said Letters Patent is hereby corrected as shown below:

Column 22, line 19, change "(1981)" to read --76 (1981)--; change "Muller" to read --Mueller--;

line 47, change "4 and 5" to read --4, 5 and 6--.

Column 23, line 67, change "to" to read --at--.

Signed and Sealed this

Fifth Day of February, 1991

*Attest:*

HARRY F. MANBECK, JR.

*Attesting Officer*       *Commissioner of Patents and Trademarks*